(12) United States Patent
Hammer et al.

(10) Patent No.: US 8,187,326 B2
(45) Date of Patent: May 29, 2012

(54) ATTACHMENT OF ABSORBABLE TISSUE SCAFFOLDS TO FIXATION DEVICES

(75) Inventors: Joseph J. Hammer, Bridgewater, NJ (US); Joseph H. Contiliano, Stewartsville, NJ (US); Murty N. Vyakarnam, New York, NY (US); Kelly R. Brown, Hillsborough, NJ (US)

(73) Assignee: Advanced Technologies and Regenerative Medicine, LLC., Raynham, MA (US)

( * ) Notice: Subject to any disclaimer, the term of this patent is extended or adjusted under 35 U.S.C. 154(b) by 0 days.

(21) Appl. No.: 10/154,136

(22) Filed: May 22, 2002

(65) Prior Publication Data

US 2003/0220700 A1    Nov. 27, 2003

(51) Int. Cl.
*A61F 2/28* (2006.01)
(52) U.S. Cl. ..................................... 623/16.11
(58) Field of Classification Search .... 623/23.72–23.76, 623/13.14, 13.15, 20.17, 23.56, 23.58, 16.11, 623/23.6–23.63, 18.11, 14.12, 17.11, 17.16, 623/11.11; 606/60, 246–249, 151, 154; 156/308.2
See application file for complete search history.

(56) References Cited

U.S. PATENT DOCUMENTS

| | | | |
|---|---|---|---|
| 4,060,081 A * | 11/1977 | Yannas et al. ............... | 623/15.12 |
| 4,186,448 A | 2/1980 | Brekke | |
| 4,927,632 A * | 5/1990 | Wong ............................ | 424/422 |
| 5,059,123 A * | 10/1991 | Jernberg ........................ | 433/215 |
| 5,067,964 A | 11/1991 | Richmond et al. | |
| 5,133,755 A | 7/1992 | Brekke | |
| 5,152,791 A * | 10/1992 | Hakamatsuka et al. ... | 623/23.56 |
| 5,306,311 A | 4/1994 | Stone et al. | |
| 5,314,478 A | 5/1994 | Oka et al. | |
| 5,466,262 A | 11/1995 | Saffran | |
| 5,492,697 A | 2/1996 | Boyan et al. | |
| 5,514,378 A | 5/1996 | Mikos et al. | |
| 5,522,895 A | 6/1996 | Mikos | |
| 5,607,474 A * | 3/1997 | Athanasiou et al. ........ | 623/23.71 |
| 5,624,463 A | 4/1997 | Stone et al. | |
| 5,629,077 A * | 5/1997 | Turnlund et al. ............. | 623/1.15 |
| 5,632,745 A * | 5/1997 | Schwartz ........................ | 606/75 |
| 5,658,582 A | 8/1997 | Dorigatti et al. | |
| 5,677,355 A | 10/1997 | Shalaby et al. | |
| 5,686,091 A * | 11/1997 | Leong et al. .................. | 424/426 |
| 5,700,289 A * | 12/1997 | Breitbart et al. .............. | 424/423 |
| 5,711,960 A | 1/1998 | Shikinami | |
| 5,713,374 A | 2/1998 | Pachence et al. | |
| 5,723,508 A | 3/1998 | Healy et al. | |

(Continued)

FOREIGN PATENT DOCUMENTS

EP      274849      7/1998

(Continued)

OTHER PUBLICATIONS

Ethicon, Inc.—ETH-1535, U.S. Appl. No. 10/159,178.

(Continued)

*Primary Examiner* — Alvin J Stewart
(74) *Attorney, Agent, or Firm* — Roberts Mlotkowski Safran & Cole, P.C.

(57) ABSTRACT

The present invention relates to tissue scaffold implant devices useful in the repair and/or regeneration of diseased and/or damaged musculoskeletal tissue and that include a tissue scaffold component fixedly attached to a scaffold fixation component via a polymeric adhesive layer, and to methods of making such tissue scaffold implant devices.

6 Claims, 2 Drawing Sheets

U.S. PATENT DOCUMENTS

| | | | |
|---|---|---|---|
| 5,749,874 A * | 5/1998 | Schwartz | 606/75 |
| 5,755,792 A | 5/1998 | Brekke | |
| 5,769,899 A * | 6/1998 | Schwartz et al. | 606/77 |
| 5,770,193 A | 6/1998 | Vacanti et al. | |
| 5,795,790 A * | 8/1998 | Schinstine et al. | 435/382 |
| 5,833,979 A * | 11/1998 | Schinstine et al. | 424/93.21 |
| 5,885,829 A * | 3/1999 | Mooney et al. | 435/325 |
| 5,899,939 A * | 5/1999 | Boyce et al. | 623/16.11 |
| 5,972,385 A | 10/1999 | Liu et al. | |
| 6,013,853 A * | 1/2000 | Athanasiou et al. | 424/423 |
| 6,031,148 A * | 2/2000 | Hayes et al. | 623/11.11 |
| 6,075,180 A * | 6/2000 | Sharber et al. | 623/11.11 |
| 6,123,727 A * | 9/2000 | Vacanti et al. | 424/422 |
| 6,143,293 A | 11/2000 | Weiss et al. | |
| 6,231,879 B1 * | 5/2001 | Li et al. | 424/422 |
| 6,251,143 B1 * | 6/2001 | Schwartz et al. | 623/23.72 |
| 6,306,424 B1 | 10/2001 | Vyakarnam et al. | |
| 6,333,029 B1 | 12/2001 | Vyakarnam et al. | |
| 6,355,699 B1 | 3/2002 | Vyakarnam et al. | |
| 6,365,149 B2 | 4/2002 | Vyakarnam et al. | |
| 6,454,811 B1 | 9/2002 | Sherwood et al. | |
| 6,461,628 B1 * | 10/2002 | Blanchard et al. | 424/402 |
| 6,468,314 B2 * | 10/2002 | Schwartz et al. | 623/23.72 |
| 6,514,515 B1 * | 2/2003 | Williams | 424/424 |
| 6,596,296 B1 * | 7/2003 | Nelson et al. | 424/426 |
| 6,626,945 B2 * | 9/2003 | Simon et al. | 623/17.19 |
| 6,626,950 B2 * | 9/2003 | Brown et al. | 623/23.72 |
| 6,632,246 B1 * | 10/2003 | Simon et al. | 623/14.12 |
| 6,699,287 B2 * | 3/2004 | Son et al. | 623/15.12 |
| 6,730,252 B1 * | 5/2004 | Teoh et al. | 264/178 F |
| 6,743,232 B2 * | 6/2004 | Overaker et al. | 623/13.14 |
| 6,840,962 B1 * | 1/2005 | Vacanti et al. | 623/23.76 |
| 6,867,247 B2 * | 3/2005 | Williams et al. | 523/124 |
| 6,899,915 B2 * | 5/2005 | Yelick et al. | 427/2.26 |
| 7,044,968 B1 * | 5/2006 | Yaccarino et al. | 623/16.11 |
| 7,048,753 B2 * | 5/2006 | Shalaby | 606/230 |
| 7,427,284 B2 * | 9/2008 | Seedhom et al. | 606/79 |
| 7,901,457 B2 * | 3/2011 | Truncale et al. | 623/16.11 |
| 2001/0010023 A1 * | 7/2001 | Schwartz et al. | 623/23.72 |
| 2001/0039455 A1 * | 11/2001 | Simon et al. | 623/23.51 |
| 2002/0119177 A1 * | 8/2002 | Bowman et al. | 424/423 |
| 2002/0183858 A1 * | 12/2002 | Contiliano et al. | 623/23.76 |
| 2003/0003127 A1 * | 1/2003 | Brown et al. | 424/423 |
| 2003/0004578 A1 * | 1/2003 | Brown et al. | 623/23.72 |
| 2003/0072790 A1 * | 4/2003 | Tsai et al. | 424/443 |
| 2003/0097148 A1 * | 5/2003 | Valimaa et al. | 606/213 |
| 2004/0138748 A1 * | 7/2004 | Boyer et al. | 623/16.11 |
| 2004/0230303 A1 * | 11/2004 | Gomes et al. | 623/16.11 |

FOREIGN PATENT DOCUMENTS

| | | |
|---|---|---|
| EP | 1064958 | 1/2001 |
| WO | WO 97 45532 | 4/1997 |
| WO | WO 99 47186 | 9/1999 |
| WO | WO 00 74554 A2 | 12/2000 |
| WO | WO 01 10306 | 2/2001 |

OTHER PUBLICATIONS

Ethicon, Inc.—ETH-1536, U.S. Appl. No. 09/874,218.

* cited by examiner

ATTACHMENT OF ABSORBABLE TISSUE SCAFFOLDS TO FIXATION DEVICES

FIELD OF THE INVENTION

The present invention relates to bioabsorbable tissue scaffold implant devices that facilitate repair or regeneration of diseased or damaged musculoskeletal tissue.

BACKGROUND OF THE INVENTION

Tissue engineering (TE) is the application of engineering disciplines to either maintain existing tissue structures or to enable new tissue growth. This engineering approach generally includes the delivery of a biocompatible tissue scaffold that serves as an architectural support onto which cells may attach, proliferate, and synthesize new tissue to repair a wound or defect. Preferably, the tissue scaffolds should be made of bioabsorbable materials. Bioabsorbable tissue scaffolds are absorbed by the body after the body has synthesized new tissue to repair the wound or defect. Synthetic bioabsorbable biocompatible polymers are well known in the art and include aliphatic polyesters, homopolymers, and copolymers (random, block, segmented and graft) of monomers such as glycolic acid, glycolide, lactic acid, lactide (d, l, meso and mixtures thereof), ε-caprolactone, trimethylene carbonate and p-dioxanone.

Many absorbable tissue scaffolds have been recognized for use in the repair and regeneration of tissue. Porous mesh plugs composed of polyhydroxy acid polymers such as polylactide are used for healing bone voids. More recently, other tissue engineering scaffolds have been reported. These scaffolds are manufactured by a number of different processes, including the use of leachables to create porosity in the scaffold, vacuum foaming techniques and precipitated polymer gel masses. Polymer melts with fugitive compounds that sublimate at temperatures greater than room temperature are known. Textile-based, fibrous tissue scaffolds and biocompatible, bioabsorbable foam tissue scaffolds formed by lyophilization are known. A porous, open-cell foam of polyhydroxy acids with pore sizes from about 10 to about 200 μm is used for the in-growth of blood vessels and cells. The foam also could be reinforced with fibers, yarns, braids, knitted fabrics, scrims and the like.

Articular cartilage is a tissue that covers the articulating surfaces between bones in the joints and consists of two principal phases: a solid matrix and an interstitial fluid phase. The matrix, which gives cartilage its stiffness and strength, is produced and maintained by chondrocytes. The interstitial fluid phase provides viscoelastic behavior to the cartilage tissue. In repairing articular cartilage, the tissue engineering scaffold must be fastened to the underlying bone so as not to be displaced by the movement of the joint.

Methods of repairing articular cartilage are known. One known articular cartilage repair piece includes a backing layer of non-woven, felted fibrous material which is either uncoated or covered by a coating of tough, pliable material. Means for fastening the repair piece to the underlying bone include elongated fasteners, suturing, adhesive bonding, and mechanical interlocking in an undercut portion of bone.

One attachment method to hold a biomaterial in place until healing occurs includes several steps. First, sutures are anchored through the subchondral plate into bony tissue with at least two lines emerging from the surface. The two lines are then pulled through the implant and used to secure the cartilage repair materials in place.

To avoid the need for a multi-step process, several prior works describe devices that combine scaffolds and the means for fastening the scaffolds to the underlying bone. For example, in one known prosthetic, resorbable, articular cartilage scaffold, an absorbable base component is adapted for insertion into a pilot hole into cancellous bone, permitting anchoring of the device into that bone. The scaffold is fabricated of biocompatible, bioresorbable fibers. In forming the device, some of the fibers in the scaffold are compressively forced through holes in the top of the base component to attach the scaffold to the base. This compressive force, used to attach the scaffold to the base, may damage the scaffold.

In another known bioabsorbable cartilage repair system, a porous bioabsorbable insert is held in the side walls of a support frame by means of radially, outwardly-extending flanges that pass through windows in the side walls. Though this results in a single device combining a scaffold and a means for fastening the scaffolds to underlying bone, the scaffold must be manufactured to contain the radially, outwardly-extending flanges.

Biocompatible tissue scaffolds also have been prepared from biological-based polymers such as hyaluronic acid (HA), collagen, alginates, chitosan and blends thereof. Three-dimensional porous foams and nonwoven structures of various biopolymers such as HA and collagen are known.

There are a number of tissue engineered scaffold devices that serve as architectural supports for the growth of new tissue structures. Although means for fastening these devices to the underlying bone have been described, the limits on the previously disclosed methods and devices include the need for a multistep fastening process, possible damage to the scaffold, and scaffolds that must be manufactured in very specific shapes to attach to the fastening means. Accordingly, there is a need for tissue engineering scaffold devices to be firmly affixed to hard tissue, such as bone or cartilage, wherein the scaffolds are held in place in the fixation device while tissue ingrowth occurs.

SUMMARY OF THE INVENTION

The present invention relates to tissue scaffold implant devices comprising a scaffold fixation component and a tissue scaffold component fixedly attached to the scaffold fixation component via a polymer adhesive layer and to methods of making such tissue scaffold implant devices. The adhesive layer may comprise a thermoplastic polymer or a soluble polymer and is disposed between the tissue scaffold component and the scaffold fixation component to provide fixed attachment of the scaffold and fixation components.

DETAILED DESCRIPTION OF THE INVENTION

In the repair of articular cartilage, the structure of the implant must be effective to facilitate tissue ingrowth, and the implant must have sufficient structural integrity and physical properties to facilitate ease of handling in an operating room environment.

Figure 1:
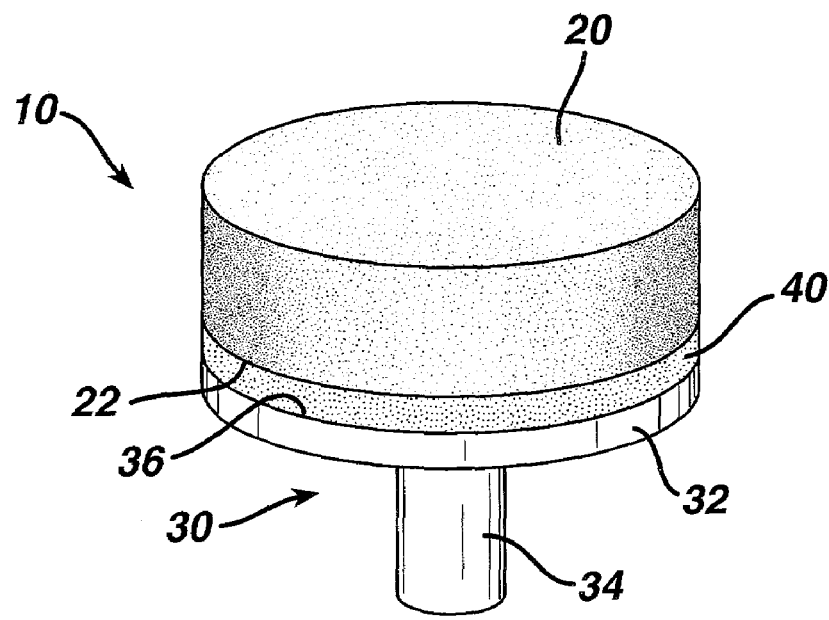
FIG. 1 is a top perspective view of a device of the present invention.
Figure 2:
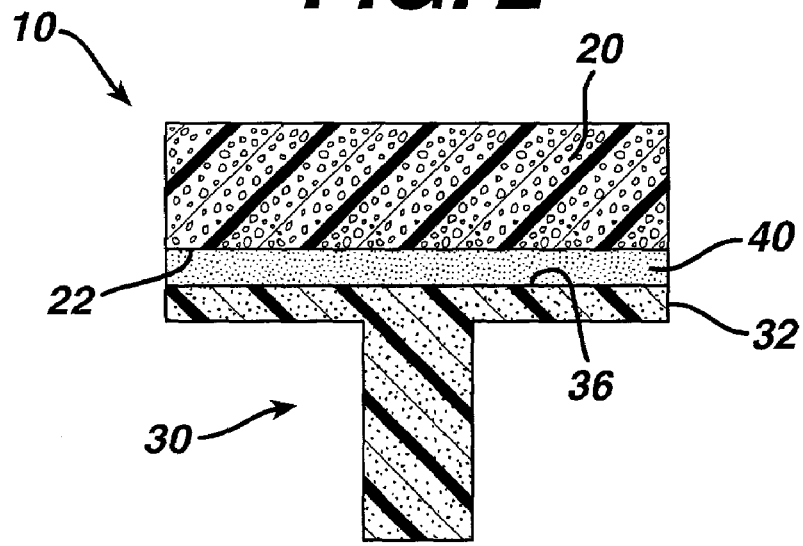
FIG. 2 is a cross-sectional view of a device of the present invention.
Figure 3:
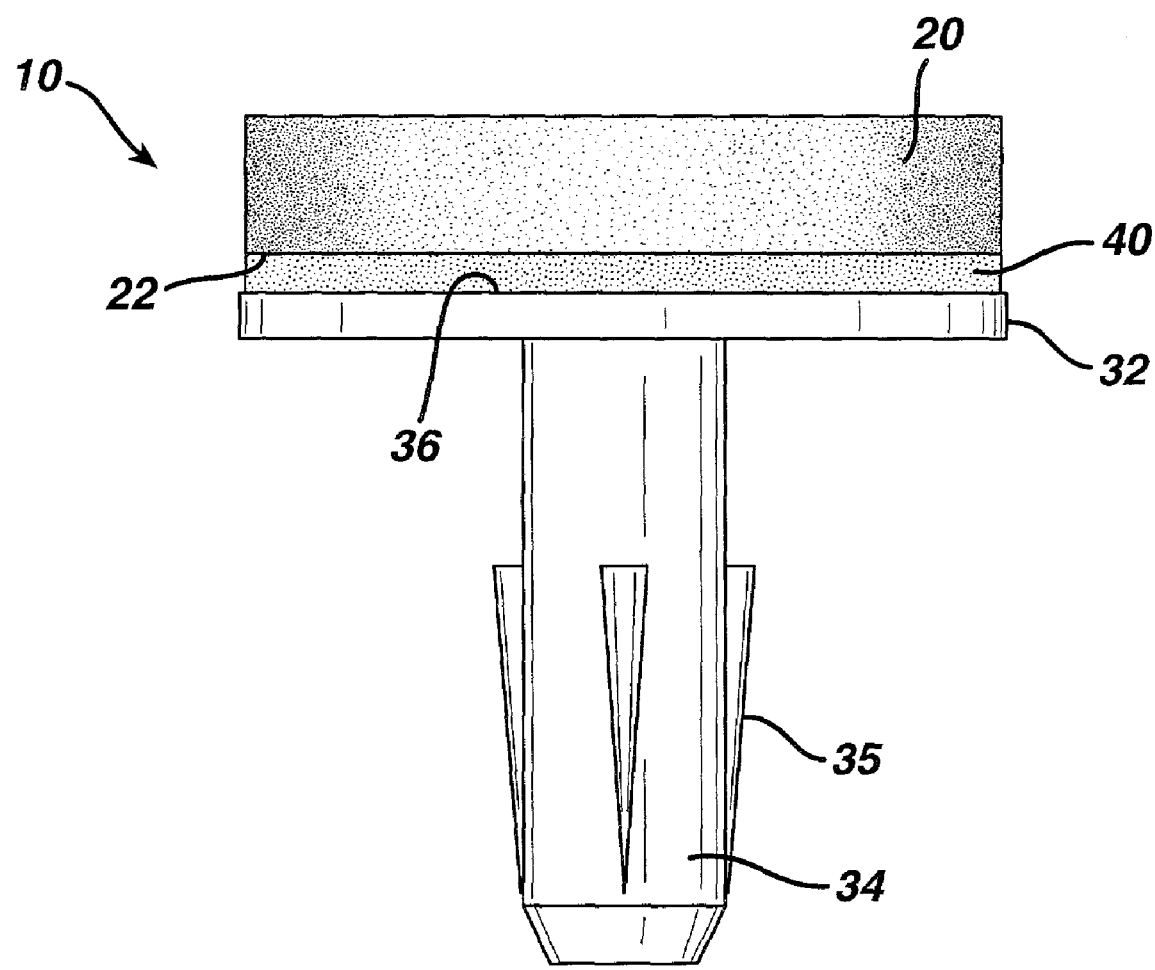
FIG. 3 is a cross-sectional view of a device of the present invention.

Referring to FIGS. 1 through 3, implant 10 includes scaffold component 20, fixation component 30, and adhesive layer 40. Fixation component 30 includes scaffold support 32 and fixation post 34. Though not shown in the figure, scaffold support 32 may have perforations therethrough to allow fluid to flow to and from scaffold component 20. It is important to note that the design of fixation component 30 is not a crucial element of the disclosed invention. Scaffold component 20 is affixed to the top surface of scaffold support 32 via adhesion layer 40.

A preferred fixation component for use in the present invention is shown in FIG. 3. As shown therein, anchoring post 34 may contain ribs, serrations, or other surface roughness or engagement means 35 that improve attachment of anchoring post 34 to the implant site.

As mentioned, implant 10 must have sufficient structural integrity and physical properties to facilitate ease of handling in an operating room environment. Polymeric foam scaffold component 20 and fixation component 30 must be fixedly attached so as to not separate before, during or after the surgical procedure. Sufficient strength and physical properties are provided in the implant through the selection of materials used to form scaffold 20, fixation component 30 and adhesive layer 40.

Adhesive layer 40 may comprise a thermoplastic or thermoset polymer, or a soluble polymer and is located between tissue scaffold component 20 and scaffold fixation component 30, and may be continuous or non-continuous. Alternatively, either tissue scaffold component 20 or scaffold fixation component 30 may comprise a thermoplastic polymer or a soluble polymer.

Adhesive layer 40 can be provided by a number of methods. In one method, the layer is created using a molten polymer and/or copolymer placed between scaffold component 20 and scaffold support 32 of fixation component 30, such that adhesive layer 40 contacts proximate surface 22 of scaffold component 20 and proximate surface 36 of fixation component 30. The molten polymer may itself stick to both of the proximate surfaces of scaffold component 20 and scaffold support 32 of fixation component 30. If the proximate surfaces of scaffold component 20 and scaffold support 32 are porous, the molten polymer may flow into the pores of either surface to create a mechanical lock between the respective proximate surfaces.

There are a number of ways to place the molten polymer on the proximate surfaces of scaffold component 20 and scaffold support 32. The molten polymer may be placed directly on one or both of the proximate surfaces, which are then brought into contact with each other. When the molten polymer cools, it solidifies, creating adhesive layer 40 between respective proximate surfaces 22 and 36.

In an alternative and preferred embodiment, the adhesive polymer may first be formed into a sheet or film, cut to a precise size and placed between proximate surface 22 of scaffold component 20 and proximate surface 36 of scaffold support 32. The assembly may then be placed in an oven and sufficiently heated to melt the adhesive polymer. The melting point of the molten polymer and/or copolymer is such that scaffold component 20 and scaffold support 32 maintain their structural integrity at this temperature, so that scaffold component 20 and scaffold support 32 are not damaged by contact with the molten polymer and/or copolymer.

If either tissue scaffold component 20 or scaffold fixation component 30 comprise a thermoplastic polymer or copolymer, an alternative method of creating adhesive layer 40 is to use a heat source to locally melt specific points of the proximate surfaces of scaffold component 20 and scaffold support 32. Heat sources for this method include, but are not limited to, soldering irons, heat guns, lasers, spot welders, ovens or ultrasonic welding devices. Once the heat source has melted the thermoplastic polymer or copolymer applied to the proximate surfaces of scaffold component 20 and scaffold support 32, the proximate surfaces are brought into contact with each other. When the molten polymer cools, it solidifies, creating adhesive layer 40 between the proximate surfaces at the specific points on the surfaces.

The integrity of scaffold component 20 and scaffold support 32 must be maintained at the temperatures needed to melt the polymers on the proximate surfaces of scaffold component 20 and scaffold support 32, so that scaffold component 20 and scaffold support 32 are not damaged by this method of creating adhesive layer 40.

If either tissue scaffold component 20 or scaffold fixation component 30 comprise a soluble polymer or copolymer, another alternative method of creating adhesive layer 40 is to use a solvent or solvents to partially dissolve the proximate surfaces of scaffold component 20 and scaffold support 32. The proximate surfaces are brought into contact and held together under pressure until the solvent evaporates. In this process, also known as solvent welding, the partially dissolved polymers or copolymers comprising the proximate surfaces of scaffold component 20 or scaffold support 32 mix when the proximate surfaces are placed in contact. When the solvent evaporates, the polymers solidify, creating adhesive layer 40 between the proximate surfaces.

The integrity of scaffold component 20 and fixation component 30 must be maintained in the presence of the solvent used to partially dissolve the soluble polymers on the respective proximate surfaces, so that scaffold component 20 and fixation component 30 are not damaged by this method of creating adhesive layer 40.

The most preferred method of creating adhesive layer 40 is to use a soluble polymer or copolymer as follows. An appropriate soluble polymer is dissolved in a solvent therefore to form a polymer solution. The solution is then spread on one or both of the proximate surfaces of scaffold component 20 and scaffold support 32, where a portion of one or both of the respective proximate surfaces are dissolved, thereby providing a polymer solution. The proximate surfaces are brought into contact and held together under pressure until the solvent evaporates. When the solvent evaporates, the polymers in the solution solidify, creating adhesive layer 40 between the proximate surfaces. The integrity of scaffold component 20 and fixation component 30 must be maintained in the presence of the solvent used, so that scaffold component 20 and scaffold support 32 are not damaged by this method of creating adhesive layer 40.

The methods of creating adhesive layer 40 between scaffold component 20 and fixation component 30 may be used on a variety of the tissue engineered scaffolds that have been reported in the art. As mentioned earlier, prior art tissue engineered scaffolds include, but are not limited to, porous mesh plugs; porous scaffolds formed by leaching, vacuum forming, or lyophilization; textile-based fibrous scaffolds, woven or non-woven; and foams reinforced with fibers, yarns, braids, knitted fabrics and scrims. A preferred scaffold component 20 for use in the present invention is nonwoven textiles.

Scaffold component 20 and fixation component 30 of the invention may comprise non-absorbable materials, such as biocompatible metals, including but not limited to stainless steel, cobalt chrome, titanium and titanium alloys; or bioinert ceramics, including but not limited to alumina, zirconia, and calcium sulfate; or absorbable glasses or ceramics comprising calcium phosphates; or autograft, allograft, or xenograft bone tissue; or non-bioabsorbable polymers, including but not limited to polyethylene, polyvinyl alcohol (PVA), polymethylmethacrylte (PMMA), silicone, polyethylene oxide (PEO), polyethylene glycol (PEG), and polyurethanes; or biocompatible and resorbable biopolymers. As used herein, the term "biopolymer" is understood to encompass naturally occurring polymers, as well as synthetic modifications or derivatives thereof. Such biopolymers include, without limitation, hyaluronic acid, collagen, recombinant collagen, cellulose, elastin, alginates, chondroitin sulfate, chitosan, chitin, keratin, silk, and blends thereof. These biopolymers can be further modified to enhance their mechanical or degradation properties by introducing crosslinking agents or changing the hydrophobicity of the side residues.

In a preferred embodiment, scaffold component 20, fixation component 30 and adhesive layer 40 comprise bioabsorbable polymers. Such a device of the present invention will result in a tissue-engineered scaffold implant device that is fully absorbable by the body and which provides and maintains structural integrity necessary for anticipated uses.

A variety of bioabsorbable polymers can be used to make tissue-engineered scaffold implant devices according to the present invention. Examples of suitable biocompatible, bioabsorbable polymers include polymers selected from the group consisting of aliphatic polyesters, polyalkylene oxalates, polyamides, polycarbonates, polyorthoesters, polyoxaesters, polyamidoesters, polyanhydrides, and polyphosphazenes.

Currently, aliphatic polyesters are among the preferred absorbable polymers for use in making the foam scaffold component according to the present invention. Aliphatic polyesters can be homopolymers or copolymers (random, block, segmented, tapered blocks, graft, triblock, etc.) having a linear, branched or star structure. Suitable monomers for making aliphatic homopolymers and copolymers may be selected from the group consisting of, but are not limited to, lactic acid, lactide (including L-, D-, meso and D,L mixtures), glycolic acid, glycolide, $\epsilon$-caprolactone, p-dioxanone (1,4-dioxan-2-one), trimethylene carbonate (1,3-dioxan-2-one), $\delta$-valerolactone, $\beta$-butyrolactone, $\epsilon$-decalactone, 2,5-diketomorpholine, pivalolactone, $\alpha,\alpha$-diethylpropiolactone, ethylene carbonate, ethylene oxalate, 3-methyl-1,4-dioxane-2,5-dione, 3,3-diethyl-1,4-dioxan-2,5-dione, $\gamma$-butyrolactone, 1,4-dioxepan-2-one, 1,5-dioxepan-2-one, 6,6-dimethyl-dioxepan-2-one and 6,8-dioxabicycloctane-7-one.

The aliphatic polyesters are typically synthesized in a ring-opening polymerization. The monomers generally are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization typically is carried out at a temperature range from about 80° C. to about 240° C., preferably from about 100° C. to about 220° C., until the desired molecular weight and viscosity are achieved.

Suitable solvents that may be used in the preparation of the tissue scaffold implant include, but are not limited to, formic acid, ethyl formate, acetic acid, hexafluoroisopropanol (HFIP), cyclic ethers (i.e. THF, DMF, and PDO), acetone, acetates of C2 to C5 alcohol (such as ethyl acetate and t-butylacetate), glyme (i.e. monoglyme, ethyl glyme, diglyme, ethyl diglyme, triglyme, butyl diglyme and tetraglyme) methylethyl ketone, dipropyleneglycol methyl ether, lactones (such as $\gamma$-valerolactone, $\delta$-valerolactone, $\beta$-butyrolactone, $\gamma$-butyrolactone) 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, the preferred solvent is 1,4-dioxane. A homogeneous solution of the polymer in the solvent is prepared using standard techniques.

In yet another embodiment of the present invention, the polymers and blends can be used as a therapeutic agent release matrix. To form this matrix, the polymer would be mixed with a therapeutic agent prior to forming the device. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; chemotherapeutic agents (i.e. anticancer agents); anti-rejection agents; analgesics and analgesic combinations; anti-inflammatory agents; hormones such as steroids; analgesics; growth factors, including bone morphogenic proteins (i.e. BMP's 2,4,6 and 12), sonic hedgehog; bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-$\beta$ I-III), vascular endothelial growth factor (VEGF); and other naturally derived or genetically engineered proteins, polysaccharides, glycoproteins, lipoproteins and cells.

Matrix materials for the present invention may be formulated by mixing one or more therapeutic agents with the polymer. Alternatively, a therapeutic agent could be coated on to the polymer, preferably with a pharmaceutically acceptable carrier. Any pharmaceutical carrier can be used that does not dissolve the polymer. The therapeutic agent may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

In another embodiment, the fixation device can be fabricated from biocompatible ceramics such as hydroxyapatite, tricalcium phosphate, or blends with biocompatible and resorbable synthetic, or metal alloys. The devices could also be made from natural materials (ie allograft bone, xenograft bone, coral etc.)

The following examples are illustrative of the principles and practice of the invention, although not limiting the scope of the invention. Numerous additional embodiments within the scope and spirit of the invention will become apparent to those skilled in the art.

In the examples, the polymers and monomers were characterized for chemical composition and purity (NMR, FTIR), thermal analysis (DSC), and molecular weight by conventional analytical techniques.

Inherent viscosities (I.V., dL/g) of the polymers and copolymers were measured using a 50 bore Cannon-Ubbelhode dilution viscometer immersed in a thermostatically controlled water bath at 25° C. utilizing chloroform or hexafluoroisopropanol (HFIP) as the solvent at a concentration of 0.1 g/dL.

In these examples certain abbreviations are used, such as PCL to indicate polymerized ε-caprolactone, PGA to indicate polymerized glycolide, PLA to indicate polymerized (L)lactide. Additionally, the percentages in front of the copolymer indicates the respective mole percentages of each constituent.

Example 1

Polymeric Melt Adhesion of the Tissue Engineering Scaffold Component to the Fixation Component Bioabsorbable fixation components were manufactured using an injection molding process. The design of the fixation component used is the same as that depicted in FIG. 3. The polymer used to manufacture the fixation components was a copolymer of 85% PLA and 15% PGA (85/15 PLA/PGA) produced by Purac (Gorinchem, The Netherlands), with an I.V. of 1.79 dL/g as measured in chloroform. The injection molder (Niigata NN35MI) had a barrel diameter of 18 mm. The hopper was fitted with a nitrogen purge to keep the polymer dry. The feed, transition and compression zone temperatures were 185° C., 185° C. and 191° C., respectively. The die and mold temperatures were 191° C. and 240° C., respectively. The maximum injection speed was 80 mm/s and maximum injection pressure was 85 Kgf/cm². The hold pressure was 70 Kgf/cm². The total time for injection and hold was 3 seconds and the cooling time at the end of hold cycle was 20 seconds. The resulting fixation components had scaffold supports that were seven millimeters in diameter.

Scaffold components were made as described below. In brief, a copolymer of PGA/PLA (90/10) was melt-extruded into continuous multifilament yarn by conventional methods of making yarn and subsequently oriented in order to increase strength, elongation, and energy required to rupture. The yarns comprised filaments of approximately 20 microns in diameter. These yarns were then cut into uniform 0.5 inch lengths to form 0.5 inch staple fiber.

Medical grade PCL (Birmingham Polymers, Inc., Birmingham, Ala.) was ground and sieved through a screen in order to filter out particles greater than 150 μm in size.

A wet lay nonwoven matrix was then prepared utilizing the 90/10 PGA/PLA copolymer staple fibers and the PCL powder. Twelve grams of staple fiber and 6.0 grams of PCL powder were dispersed into 1,926 cubic inches of water. The water was agitated to promote a uniform mixture. Processing aids were added to the water to allow a uniform dispersion of the filaments within the water without causing foaming. Processing aids used included 117 grams Nalco 625 liquid polymer (Nalco Chemical Company, Naperville, Ill.), 20 drops Value M-20 (Marubishi Oil Company, Limited, Osaka, Japan), and 5 drops Berchem 4283 (Bercen, Incorporated, a division of Cranston Print Works Company, Cranston, R.I.).

Once the fibers were uniformly dispersed within the water, the mixture was drained through a screen. This screen allows water to pass through, but traps the fibers and PCL powder. After the water drained through the screen, the mat of fibers and PCL powder was removed. The mat was then placed in a container of water heated to approximately 80° C. in order to melt the PCL. The melt temperature of the particular PCL used ranges between about 60° C. and about 80° C.

The mat was rinsed overnight in water followed by another overnight incubation in ethanol to remove any residual chemicals or processing aids used during the manufacturing process.

A bioabsorbable 65/35 copolymer of PLA/PGA (Ethicon, Inc. Cornelia, Ga.) was compression molded into a thin sheet. A hot press (Tetrahedron Model 1401, Tetrahedron Associates, Inc., San Diego, Calif.), set at 100° C. and 20,000 pounds of force, was used to form the sheet under a nitrogen environment. The press was shimmed to a height of 0.003 inches. Compressing the copolymer under these conditions yielded a film with a thickness of between 0.003 and 0.004 inches.

This film was used to attach the scaffold component to the fixation component as follows. Seven millimeter diameter disks of the copolymer film and scaffold component were cut using a steel ruled die. The film disk was stacked between the scaffold support of the fixation component and the scaffold component. A weight of between 15 and 16 grams was added to compress the device during subsequent processing. The assembly was then placed in a nitrogen purged oven set at 80° C. for 2 hours. This temperature was sufficient to allow the film disk to melt and flow, but not adversely effect the fixation or scaffold components. After 2 hours, the implant was removed from the oven and allowed to cool for a minimum of 15 minutes prior to handling. When the weight was removed, the scaffold component was bonded to the fixation component.

Example 2

PLA/PGA Copolymer/Solvent Solution Adhesion of the Tissue Engineering Scaffold to the Fixation Device Seven millimeter diameter disks of scaffold component were prepared as discussed in Example 1. Fixation components with scaffold supports that were seven millimeters in diameter were also prepared as discussed in Example 1.

A bioabsorbable 85/15 copolymer of PLA/PGA (produced by Purac Biochem, the Netherlands) was dissolved in ethyl acetate. A five percent weight copolymer solution was obtained by heating the solution at approximately 60° C. during gentle agitation.

The scaffold component was placed on the scaffold support of the fixation component. A disk of PTFE (poly(tetrafluoroethylene)) was placed on the scaffold component. The scaffold component was then saturated with the copolymer solution. A weight of between 15 and 16 grams was applied to the PTFE disk to hold the scaffold component firmly against the scaffold support. The solution was then allowed to dry in air overnight. After the drying cycle, the scaffold component released easily from the PTFE disk, and was firmly attached to the fixation component.

Example 3

PCL/PLA Copolymer/Solvent Solution Adhesion of the Tissue Engineering Scaffold to the Fixation Device Seven millimeter diameter disks of scaffold component were prepared as discussed in Example 1. Fixation components with scaffold supports that were seven millimeters in diameter were also prepared as discussed in Example 1.

A bioabsorbable 40/60 copolymer of PCL/PLA (produced by Birmingham Polymers, Birmingham, Ala.) was dissolved in ethyl acetate. A five percent weight copolymer solution was obtained by heating the solution at approximately 60° C. during gentle agitation.

The scaffold component was placed on the scaffold support of the fixation component. A disk of PTFE (poly(tetrafluoroethylene)) was placed on the scaffold component. The scaffold component was then saturated with the copolymer solution. A weight of between 15 and 16 grams was applied to the PTFE disk to hold the scaffold component firmly against the scaffold support. The solution was then allowed to dry in air overnight. After the drying cycle, the scaffold component released easily from the PTFE disk, and was firmly attached to the fixation component.

We claim:

1. A tissue scaffold implant device, comprising:
   a non-woven textile tissue scaffold component having a top surface and a bottom surface, the tissue scaffold component comprising a soluble polymer,
   a tissue scaffold support, having a top surface and a fixation post integral therewith and extending opposite from said top surface, the tissue scaffold support comprising a soluble thermoplastic polymer, and
   an adhesive layer between said scaffold component and said top surface of said tissue scaffold support, said adhesive layer comprising a soluble polymer having a top surface and a bottom surface, the bottom surface of the scaffold component is fixedly attached to the top surface of the adhesive layer and the bottom surface of the adhesive layer is fixedly attached to the top surface of the scaffold support,
   and
   said soluble polymer of the tissue scaffold component is selected from the group consisting of polyalkylene oxalates, polyamides, polycarbonates, polyorthoesters, polyoxaesters, polyamidoesters, polyanhydrides and polyphosphazenes, and aliphatic polyesters selected from the group consisting of glycolide, ε-caprolactone, p-dioxanone (1,4-dioxan-2-one), trimethylene carbonate (1,3-dioxan-2-one), δ-valerolactone, β-butyrolactone, ε-decalactone, 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, γ-butyrolactone, 1,4-dioxepan-2-one, 1,5-dioxepan-2-one, 6,6-dimethyl-dioxepan-2-one and 6,8-dioxabicycloctane-7-one.

2. The device of claim 1 wherein said adhesive layer soluble polymer is thermoplastic.

3. The device of claim 1, wherein the top surface of said tissue scaffold support is non-porous.

4. The device of claim 1, wherein the scaffold support comprises a biocompatible ceramic.

5. The device of claim 1, wherein the tissue scaffold component and the scaffold support comprise different bioabsorbable polymers.

6. The device of claim 5, wherein the tissue scaffold component is a wet-laid nonwoven textile comprising 90 mole % PGA/10 mole % PLA copolymer fibers and the scaffold support comprises 85 mole % PLA/15 mole % PGA copolymer.

\* \* \* \* \*